United States Patent
Dawkes et al.

(12)

(10) Patent No.: US 6,197,533 B1
(45) Date of Patent: *Mar. 6, 2001

(54) CHEMICAL MODIFICATION OF ANTIBODIES AND ANTIGENS

(75) Inventors: Adrian Charles Dawkes, Berks; John Arthur Diment, Bucks; Graham DeLisle Yearwood, London, all of (GB)

(73) Assignee: Ortho-Clinical Diagnostics, Inc., Rochester, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/386,390

(22) Filed: Feb. 10, 1995

(30) Foreign Application Priority Data

Feb. 19, 1994 (GB) .................................... 9403215

(51) Int. Cl.[7] ....................... G01N 33/531; G01N 55/545
(52) U.S. Cl. .......................... 435/7.94; 435/962; 436/500; 436/811; 436/825
(58) Field of Search .................... 436/811, 500, 436/825; 435/7.94, 962

(56) References Cited

U.S. PATENT DOCUMENTS 4,914,040 * 4/1990 Lenz et al. .................. 436/175
5,484,706 * 1/1996 Peterson et al. .............. 435/7.36

FOREIGN PATENT DOCUMENTS 2 278 195   11/1994 (GB) .

OTHER PUBLICATIONS

R. O'Brien et al., Archives of Biochemistry and Biophysics, vol. 310, No. 1, pp. 25–31, Apr. 1994.*
Marques et al., Journal of Biological Chemistry, vol. 268, No. 14, pp. 10393–10402 (1993).*
Nag et al., Journal of Biological Chemistry, vol. 266, No. 17, pp. 11116–11121 (1991).*
Victoria et al., Molecular Immunology, vol. 23, No. 10, pp. 1039–1044 (1986).*
Gudmundsson et al., Journal of Immunological Methods, vol. 158, pp. 215–227 (1993).*
Meyer, et al., Biochemistry, vol. 19, pp. 1874–1881 (1980).*
B.E. Gudmundsson, N. M. Young, R. P. Oomen.: "Characterisation of Residues in Antibody Binding Sites by Chemical Modification of Surface–Adsorbed Protein Combined with Enzyme Immunoassay" J. of Immunological Methods, 158:2, pp. 215–227, Mar. 2, 1993.
S. P. Kessler and D. R. Gallaway: "Pseudomonas Aeruginosa Exotoxin A Interactin with Eucaryotic Elongation Factor 2" J. of Biological Chemistry, 267:27, pp. 19107–19111, Sep. 25, 1989.
K. P. Willey and F. Leidenbeger: "Functionally Distinct Agonist and Receptor–Binding Regions in Human Chorionic Gonadotropin" J. of Biological Chemistry, 264:33, pp. 19716–19729, Nov. 25, 1989.

* cited by examiner

Primary Examiner—Mary E. Ceperley

(57) ABSTRACT

There is described a method for the chemical modification of antibodies and/or antigens in order to minimise sample interference in immunoassays, an immunoassay method in which chemically modified antibodies and/or antigens are employed, the use of chemically modified antibodies and/or antigens in an immunoassay and a kit for assaying biological specimens which comprises the chemically modified antibodies and/or antigens.

4 Claims, 2 Drawing Sheets

CHEMICAL MODIFICATION OF ANTIBODIES AND ANTIGENS

This invention relates to a method for the chemical modification of antibodies and/or antigens in order to minimise sample interference in immunoassays, to an immunoassay method in which chemically modified antibodies and/or antigens are employed, to the use of the chemically modified antibodies and/or antigens in an immunoassay and to a kit for assaying biological specimens which comprises the chemically modified antibodies and/or antigens.

Sample interference in immunoassays involves deleterious interactions between specific components of immunoassays and interfering species in samples and is a well documented phenomenon. References to sample interference include (1) Levinson S., "Heterophilic antibodies and their role in immunoassay interference"; J. Clin. Immunoassay, 1992, 15, 108–115 and (2) Maxey K. M., Krishna R. M and Birkmeir J., "Interference in Enzyme Immunoassays"; J. Clin. Immunoassay, 1992 15, 116–120. Much of this interference can be attributed to the presence of species within samples that cross-link specific immunoassay components. Routinely this is caused by antibodies or other sample components that are directed against either (a) structural elements of the immunoglobulins of the immunoassay or (b) structural elements of native, recombinant or synthetic antigens.

Immunoglobulins are constructed from two heavy chains each consisting of three constant regions (CH-1, CH-2 and CH-3) and a variable region (VH). These are associated with two light chains each consisting of a constant region (CL) and a variable region (VL). There are also structural variants of immunoglobulin heavy and light chains termed isotypes—see for example Vlug A. and Van Remortal P., "The structure and function of human IgG subclasses"; European Clinical Lab., 1989, 8, 26–33. An interfering sample may show reactivity against one isotype but not another. Other interfering samples may show reactivity across isotypes. A significant proportion, although not all, of the interfering anti-antibody components are directed against the Fc region (CH2–CH3) of the assay specific immunoglobulins. Interference can also occur when labelled and unlabelled assay specific species, where one or more of these is the antigen, are cross-linked by an interfering species. Blocking of interference has been achieved in the past by addition of quantities of immunoglobulin containing sera from different species or purified immunoglobulins or aggregated immunoglobulins. This has been described in U.S. Pat. No. 4,914,040 to Boehringer Mannheim issued 1990 and entitled "Reagent and method for determination of a polyvalent substance using an immunoaggregate". Reduction of the interference has also been achieved by removal of the Fc fragment from one or more of the assay specific immunoglobulins and also by blocking assay specific antibody with anti FC antibody as described in European Patent Publication No. 566205A.

It has been reported that rheumatoid factor and other interfering species are predominantly reactive with the CH-2 and CH-3 regions on immunoglobulin heavy chains—see for example Williams R. C., Malone C. and Solomon A., "Conformational dependency of human IgG heavy chain-associated Gm allotypes"; Mol. Immunol., 1993, 30, (4), 341–351. The existance of species reactive with the CH1 region of immunoglobulin heavy chains is also known—see for example Aguado M. T., Balderas R. S., Rubin R. L., Duchosal R. K., Kofler R., Birshtein B. K., Secher D. S., Dixon F. J. and Theofilopoulos A. N., "Specificity and molecular characteristics of monoclonal IgM rheumatoid factors from arthritic and non-arthritic mice"; J. Immunol., 1987, 139, 1080–1087. The presence of these factors in sample sera can cause incorrect antigen concentration determinations in immunoassays. Removal of the Fc from assay specific immunoglobulins will therefore not prevent factors reactive with the CH-1 region from binding.

According to the present invention we provide a method for the chemical modification of antibodies and/or antigens and/or fragments of antibodies and/or antigens characterised in that at least one amino acid selected from the group consisting of argenine, histidine, lysine, threonine and tyrosine located at an active site within the antibody, antigen and/or fragment thereof is modified by chemical treatment in such a manner that recognition of the antibody, antigen and/or fragment thereof by an interfering antibody is substantially prevented.

Further according to the present invention we provide a method for the immunoassay of a biological specimen which comprises a step in which there is used an antibody and/or antigen and/or a fragment of an antibody and/or antigen characterised in that the antibody and/or antigen and/or fragment thereof has at least one amino acid selected from the group consisting of argenine, histidine, lysine, threonine and tyrosine located at an active site within the antibody, antigen and/or fragment thereof which has been modified by chemical treatment in such a manner that recognition of the antibody, antigen and/or fragment thereof by an interfering antibody is substantially prevented.

Further according to the present invention we provide the use in a method for the immunoassay of a biological specimen of a modified antibody and/or antigen and/or fragment of an antibody and/or antigen characterised in that the antibody and/or antigen and/or fragment thereof has at least one amino acid selected from the group consisting of argenine, histidine, lysine, threonine and tyrosine located at an active site within the antibody, antigen and/or fragment thereof which has been modified by chemical treatment in such a manner that recognition of the antibody, antigen and/or fragment thereof by an interfering antibody is substantially prevented.

Further according to the present invention we provide a kit useful in an immunoassay which comprises an antibody and/or antigen and/or fragment of an antibody and/or antigen characterised in that the antibody and/or antigen and/or fragment thereof has at least one amino acid selected from the group consisting of argenine, histidine, lysine, threonine and tyrosine located at an active site within the antibody, antigen and/or fragment thereof which has been modified by chemical treatment in such a manner that recognition of the antibody, antigen and/or fragment thereof of an interfering antibody is substantially prevented.

The chemical modification of specific amino acid residues in the immunoglobulin or antigen enables blocking or reduction of the interactions mentioned above and other non-desirable interactions in the case of antigens to be achieved. Suitably the antibody, antigen and/or fragment (hereinafter referred to as the reagent particle) is chemically treated to modify the charge and/or structural properties of one or more of the group of amino acids concerned ie argenine, histidine, lysine, threonine and tyrosine so that recognition by the reagent particle of an interfering antibody is no longer possible. Suitably the active sites on the reagent particle which are targeted for modification of amino acids are those areas to which an interfering amino acid could bind to a significant extent. Preferred target regions of the reagent particle include the "constant" regions of antibodies ie the CH 1, CH 2 and CH 3 regions and between the CH 2 and CH 3 regions. Preferably, during the modification method, argenine, histidine, lysine, threonine and tyrosine moeties located on a reagent particle elsewhere than at active sites are protected in a manner suitable to prevent any significant modification of them from occurring.

Any suitable chemical modification of the amino acid moeties concerned on the reagent particle may be used in the modification method of the invention. The preferred modification technique in any instance will depend upon the amino acid to be modified.

Chemical compounds which can be used to modify reagent particles include compounds having the structure:

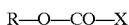

where R can be any of a wide range of groups including alkyl, aryl and pyridyl; and X is a leaving group such as pyrocarbonate

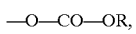

a halogen group, particularly a chloride or a bromide or a mixed acid anhydride such as

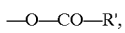

where R' can be any one of a wide range of alternatives (compounds of this structure are particularly useful for the modification of histidine or lysine moeties);

Alkyl halides; and

Compounds having the structures:

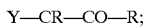

and

where R is as before, having a wide range of possibilities;

Y is suitably an acid group, an activating ester group or a halogen group particularly chloride or bromide; and Z is a halogen group.

The chemical compound used in the modification method can also be a precursor of that used to effect the modification, ie a source of suitable radicals. An example of such a precursor is diazomethane.

Specific compounds which can be used include N-benzyloxycarbonyloxy succinimide, N-(2-bromobenzyloxycarbonyloxy) succinimide, diphenylcarbamyl chloride and adamantyl fluoroformate.

Compounds particularly suitable for the modification method of the invention in a wide range of instances are pyrocarbonates having the structure:

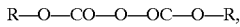

where R can vary greatly, possible groups including aryl, alkyl and pyridyl.

Particularly suitable pyrocarbonates include dimethylpyrocarbonate diethylpyrocarbonate and dipropylpyrocarbonate.

Suitable conditions for the modification process of the invention depend on the reagent particle, the chemical modifier used, the amino acid group to be modified and its location in the reagent particle, ie the target region. Suitably the pH is selected to take account of the target site and the chemical reagent used to effect the modification. The temperature affects the specificity of the modification achieved and is suitably controlled to obtain suitable specificity. Greater specificities are achieved at lower temperatures.

The invention is generally applicable to immunoassays including assays for TSH, Toxo IgG, Toxo IgM, Rubella and free hormone assays. Very suitably the modified antibody and/or antigen is supplied as conjugate together with an enzyme marker such as horse radish peroxidase (HRP).

The invention gives the advantage of reduced sample interference in the operation of immunoassays.

The invention is illustrated by the following Examples and by the accompanying drawings wherein.

EXAMPLE 1

A horseradish peroxidase conjugated anti-TSH antibody (anti-TSH-HRP) was pretreated with 34 mMolar diethylpyrocarbonate in 0.1 molar phosphate buffer at pH 6.0 for 30 minutes at room temperature. The thus pretreated and modified anti-TSH-HRP was then diluted to 0.42 ug/ml in a phosphate buffer containing 1% w/v Bovine Serum Albumin. This was then incubated with a euthyroid serum known to contain an interfering species in immunoassay wells coated with a second anti-TSH antibody. Unmodified anti-TSH-HRP was included in the experiment as a control. The incubation was carried out for 30 minutes at 37° C. on an "Amerlite" (TM) shaker incubator marketed by Kodak Clinical Diagnostics Limited (KCDL), Mandeville House, 62 The Broadway, Amersham, Buckinghamshire, HP7 0HJ, UK. After this the wells were washed and "Amerlite" Signal Generation Reagent (also marketed by KCDL) was added. The level of signal and data integration for each sample was determined on an "Amerlite" Analyser (also marketed by KCDL). The experiment was carried out generally in the manner described in the pack leaflet of the standard test for anti-TSH antibody marketed by KCDL.

The results were as follows:

TSH measured using unmodified antibody 9.37 mIU/ml= Hypothyroid

TSH measured using modified antibody 0.23 mIU/ml= Euthyroid

EXAMPLE 2

Figure 1:
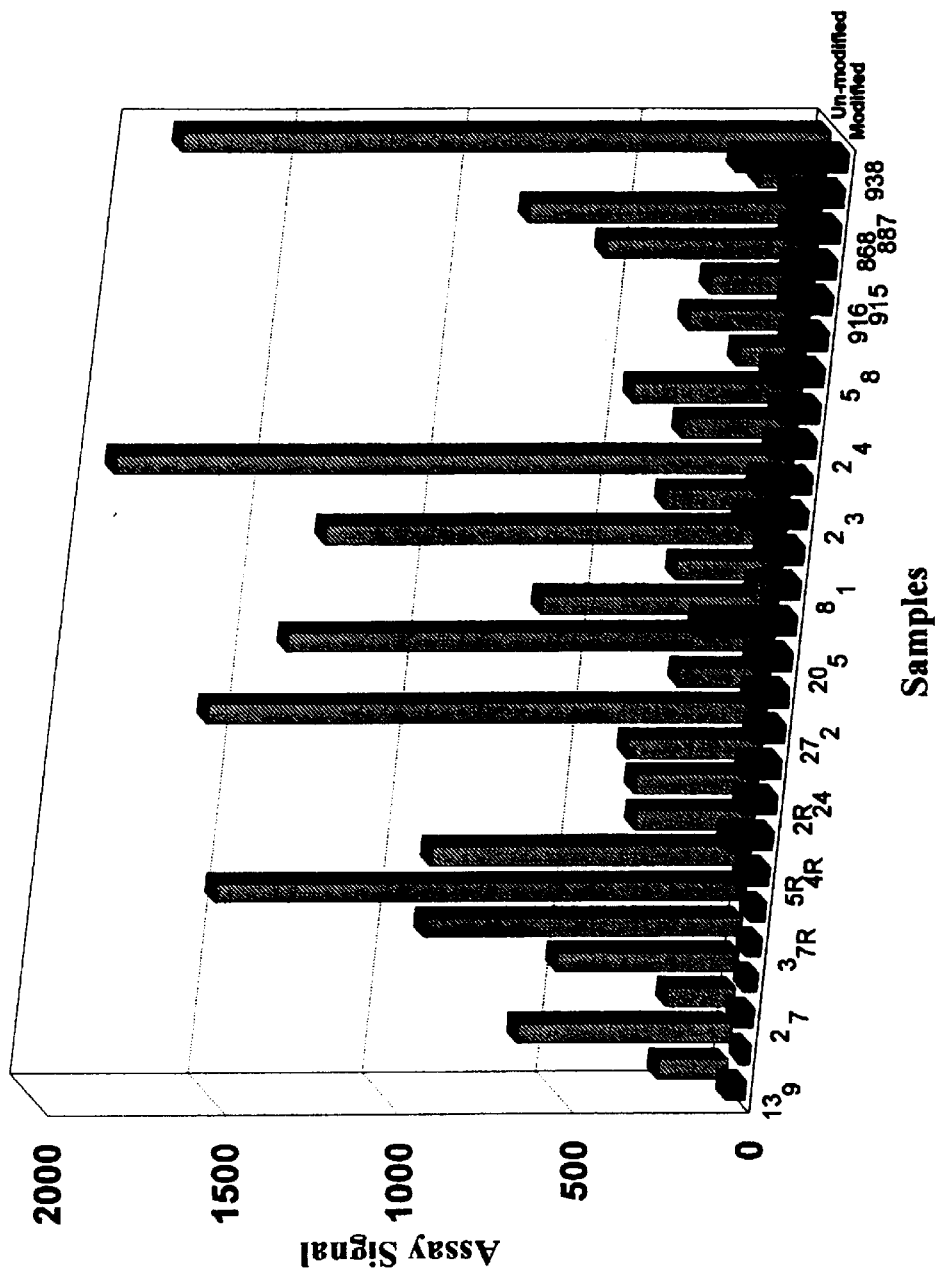
FIG. 1 is a block diagram illustrating the results of Example 2.

This was carried out using experimental conditions which were identical with those of Example 1 save for the modification described hereafter. Example 1 was modified in that 29 known rheumatoid positive samples all known to be euthyroid were diluted 1 in 10 and assayed using either modified or unmodified anti-TSH-HRP antibody. The results are set out in FIG. 1 which is a block diagram comparing the intensities of the light signals in Light Units for modified and unmodified samples. FIG. 1 shows that the intensities of the interfering signals for the unmodified samples are significantly greater than those of the modified samples.

EXAMPLE 3

The preservation of the antigen binding capability of a modified anti-TSH-HRP antibody was demonstrated by incubating a range of concentrations of TSH in anti-TSH antibody coated wells in the presence of either a modified or an unmodified anti-TSH-HRP antibody. The quantity of TSH measured in each system was then determined from signal outputs after addition of "Amerlite" (TM) Signal Generation Reagent.

Figure 2:
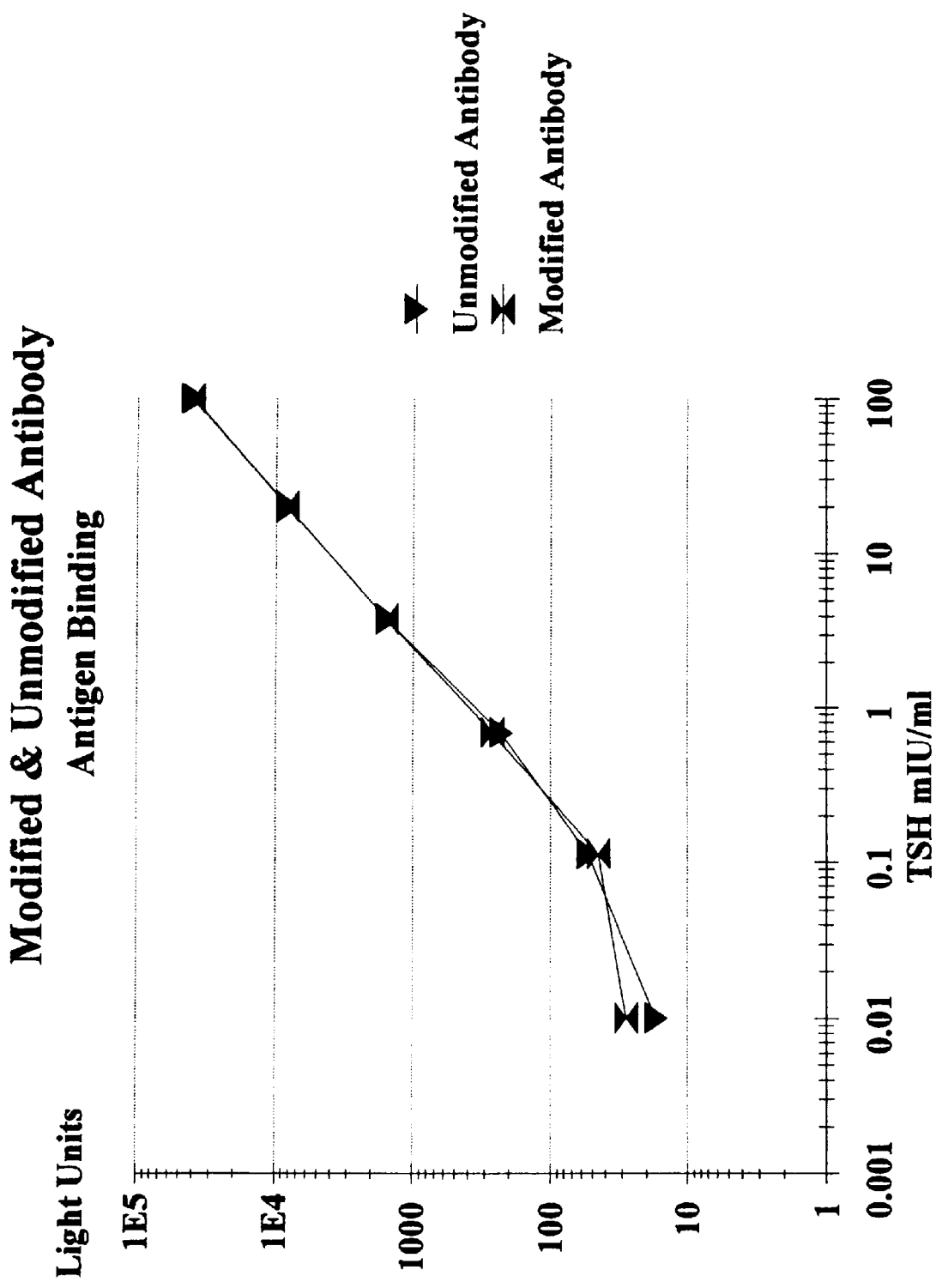
FIG. 2 is a graph illustrating the results of Example 3.

FIG. 2, which is a graph of signal intensity against TSH concentration in mIU/ml, compares the antigen binding capability of the modified and unmodified wells. It can be seen from FIG. 2 that there is no significant difference between the antigen binding capabilities of the modified and unmodified antibodies.

EXAMPLE 4

Modification of the antigen using diethylpyrocarbonate was carried out by the following method. "Amerlite" (TM) HIV 1 and 2 assay wells were pretreated with 0.45 mM diethylpyrocarbonate in phosphate buffered saline solution at pH 7.4 for 15 minutes. The wells were washed with a Tris/Sucrose/Saline/BSA solution and dried before use. HIV negative samples that were known to contain interfering species were selected and assayed using modified and unmodified wells in the "Amerlite" (TM) HIV 1 and 2 assay.

The numbers of reactive samples on modified and unmodified wells were as follows;

unmodified wells
 11/11
modified wells
 2/11

What is claimed is:

1. A method for minimizing interference in an immunoassay of a serum sample comprising, chemically modifying an amino acid located in an active site within an antibody, antigen, or fragment thereof to be used as a component of the immunoassay, wherein said amino acid is selected from the group consisting of: arginine, histidine, lysine, threonine, and tyrosine, by treating said amino acid with a compound selected from the group consisting of: R—O—CO—X; alkyl halide; Y—CR—CO—R; R—CO—Y; and R—NCO—Z and precursors thereof wherein R is alkyl, aryl, or pyridyl, X is a leaving group, —O—CO—OR, a halogen, or a mixed acid anhydride, Y is an acid group, an activating ester group, or a halogen; and Z is a halogen such that recognition of said modified antibody, antigen, or fragment thereof by an interfering antibody is substantially prevented.

2. The method of claim 1 wherein the modified antibody or fragment thereof recognizes an analyte selected from the group consisting of: thyroid stimulating hormone, Toxo IgG, Toxo IgM, rubella, and free hormone.

3. The method of claim 1 wherein the modified antigen or fragment thereof is a human immunodeficiency virus 1 or 2 antigen.

4. A kit for an immunoassay for the determination of an analyte in serum comprising, a composition comprising an antibody, antigen, or fragment thereof, which will recognize the analyte but which has an amino acid which has been chemically modified in an active site by a reagent comprising a compound selected from the group consisting of: R—O—CO—X; alkyl halide; Y—CR—CO—R; R—CO—Y; and R—NCO—Z and precursors thereof wherein R is alkyl, aryl, or pyridyl, X is a leaving group, —O—CO—OR, a halogen, or a mixed acid anhydride, Y is an acid group, an activating ester group, or a halogen; and Z is a halogen;

wherein said amino acid is selected from the group consisting of: arginine, histidine, lysine, threonine, and tyrosine.

* * * * *